US009725690B2

(12) United States Patent
Presz, Jr. et al.

(10) Patent No.: US 9,725,690 B2
(45) Date of Patent: *Aug. 8, 2017

(54) FLUID DYNAMIC SONIC SEPARATOR

(71) Applicant: FloDesign Sonics, Inc., Wilbraham, MA (US)

(72) Inventors: Walter M. Presz, Jr., Wilbraham, MA (US); Bart Lipkiens, Hampden, MA (US); Jason Dionne, Simsbury, CT (US); Thomas J. Kennedy, III, Wilbraham, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 528 days.

This patent is subject to a terminal disclaimer.

(21) Appl. No.: 14/313,813

(22) Filed: Jun. 24, 2014

(65) Prior Publication Data

US 2014/0377834 A1     Dec. 25, 2014

Related U.S. Application Data

(60) Provisional application No. 61/838,432, filed on Jun. 24, 2013.

(51) Int. Cl.
*B01D 21/28* (2006.01)
*C12M 1/00* (2006.01)
(Continued)

(52) U.S. Cl.
CPC .......... *C12M 47/02* (2013.01); *B01D 21/283* (2013.01); *B06B 1/0644* (2013.01); *C12N 13/00* (2013.01)

(58) Field of Classification Search
CPC ...... C12M 47/02; C12M 29/18; C12M 29/10; C12M 33/08; C12M 35/04; C12N 13/00;
(Continued)

(56) References Cited

U.S. PATENT DOCUMENTS

| 2,667,944 A | 2/1954 | Crites |
| 3,555,311 A | 1/1971 | Weber |

(Continued)

FOREIGN PATENT DOCUMENTS

| DE | 30 27 433 A1 | 2/1982 |
| EP | 0 292 470 B1 | 11/1988 |

(Continued)

OTHER PUBLICATIONS

International Search Report for PCT/US2014/043930 dated Oct. 22, 2014.

(Continued)

*Primary Examiner* — Walter D Griffin
*Assistant Examiner* — Cameron Allen
(74) *Attorney, Agent, or Firm* — Richard M. Klein; Fay Sharpe LLP

(57) ABSTRACT

An acoustic standing wave is utilized to separate components from a multi-component fluid, such as animal cells from fluid-cell mixture, in a fluid flow scheme with an acoustophoresis device. For example, the flow scheme and device allows for trapping of falling cells as the cells coalesce, agglomerate, and the weight of the agglomerated mass overcomes the drag and ultrasonic standing wave forces in the device.

22 Claims, 12 Drawing Sheets

(51) Int. Cl.
*C12N 13/00* (2006.01)
*B06B 1/06* (2006.01)

(58) Field of Classification Search
CPC .......... C12N 1/02; B01D 17/04; B01D 17/06; B01D 21/283; B01D 21/28; B06B 1/0644; H01L 41/0973
See application file for complete search history.

(56) References Cited

U.S. PATENT DOCUMENTS

| | | |
|---|---|---|
| 4,055,491 A | 10/1977 | Porath-Furedi |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,398,325 A | 8/1983 | Piaget et al. |
| 4,666,595 A | 5/1987 | Graham |
| 4,699,588 A | 10/1987 | Zinn et al. |
| 4,743,361 A | 5/1988 | Schram |
| 4,759,775 A | 7/1988 | Peterson et al. |
| 4,983,189 A | 1/1991 | Peterson et al. |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,902,489 A | 5/1999 | Yasuda et al. |
| 5,912,182 A | 6/1999 | Coakley et al. |
| 5,951,456 A | 9/1999 | Scott |
| 6,090,295 A | 7/2000 | Raghavarao et al. |
| 6,166,231 A | 12/2000 | Hoeksema |
| 6,205,848 B1 | 3/2001 | Faber et al. |
| 6,216,538 B1 | 4/2001 | Yasuda et al. |
| 6,332,541 B1 | 12/2001 | Coakley et al. |
| 6,391,653 B1 | 5/2002 | Letcher et al. |
| 6,487,095 B1 | 11/2002 | Malik et al. |
| 6,592,821 B1 | 7/2003 | Wada et al. |
| 6,649,069 B2 | 11/2003 | DeAngelis |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,679,338 B2 | 3/2014 | Rietman et al. |
| 9,228,183 B2 * | 1/2016 | Lipkens ................ B01D 21/28 |
| 9,272,234 B2 * | 3/2016 | Lipkens ................ B01D 43/00 |
| 2002/0134734 A1 | 9/2002 | Campbell et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2005/0196725 A1 | 9/2005 | Fu |
| 2006/0037915 A1 | 2/2006 | Strand et al. |
| 2007/0272618 A1 | 11/2007 | Gou et al. |
| 2007/0284299 A1 | 12/2007 | Xu et al. |
| 2008/0217259 A1 * | 9/2008 | Siversson ........... A61M 1/3693 436/177 |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0098027 A1 | 4/2009 | Tabata et al. |
| 2009/0178716 A1 | 7/2009 | Kaduchak et al. |
| 2009/0194420 A1 | 8/2009 | Mariella, Jr. et al. |
| 2009/0295505 A1 | 12/2009 | Mohammadi et al. |
| 2010/0000945 A1 | 1/2010 | Gavalas |
| 2010/0078384 A1 | 4/2010 | Yang |
| 2010/0124142 A1 | 5/2010 | Laugharn et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0024335 A1 | 2/2011 | Ward et al. |
| 2011/0092726 A1 | 4/2011 | Clarke |
| 2011/0123392 A1 | 5/2011 | Dionne et al. |
| 2011/0154890 A1 | 6/2011 | Holm et al. |
| 2011/0166551 A1 | 7/2011 | Schafer |
| 2011/0262990 A1 | 10/2011 | Wang et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0328477 A1 | 12/2012 | Dionne et al. |
| 2012/0329122 A1 | 12/2012 | Lipkens et al. |
| 2013/0277316 A1 | 10/2013 | Dutra et al. |
| 2013/0284271 A1 | 10/2013 | Lipkens et al. |
| 2013/0302213 A1 * | 11/2013 | Lipkens ................ B01D 43/00 422/119 |
| 2014/0011240 A1 * | 1/2014 | Lipkens ................ B01D 21/28 435/71.1 |
| 2015/0176001 A1 * | 6/2015 | Lipkens ................ B01D 21/28 435/173.9 |

FOREIGN PATENT DOCUMENTS

| | | |
|---|---|---|
| EP | 1 254 669 B1 | 11/2002 |
| GB | 2 420 510 A | 5/2006 |
| WO | WO 87/07178 A1 | 12/1987 |
| WO | WO 02/072234 A1 | 9/2002 |
| WO | WO 2009/111276 A1 | 9/2009 |
| WO | WO 2009/144709 A1 | 12/2009 |
| WO | WO 2010/024753 A1 | 4/2010 |
| WO | WO 2011/023949 A2 | 3/2011 |
| WO | WO 2011/027146 A2 | 3/2011 |
| WO | WO 2011/161463 A2 | 12/2011 |
| WO | WO 2014/014941 A1 | 1/2014 |
| WO | WO 2014/055219 A2 | 4/2014 |

OTHER PUBLICATIONS

Alvarez et al.; Shock Waves, vol. 17, No. 6, pp. 441-447, 2008.
Benes et al.; Ultrasonic Separation of Suspended Particles, 2001 IEEE Ultrasonics Symposium; Oct. 7-10, 2001; pp. 649-659; Atlanta, Georgia.
Castro; Tunable gap and quantum quench dynamics in bilayer graphene; Jul. 13, 2010; Mathematica Summer School.

(56) References Cited

OTHER PUBLICATIONS

Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systems, Jan. 2007, pp. 359-378.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et a.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Seymour et al, J. Chem. Edu., 1990, 67(9), p. 763, published Sep. 1990.
Annex to Form PCT/ISA/206—Communication Relating to the Results of the Partial International Search Report, dated Jul. 18, 2013.
European Search Report of European Application No. 11769474.5 Dated Oct. 10, 2012.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2013/037404 Dated Jun. 21, 2013.
International Search Report and Written Opinion of International Application No. PCT/US2013/050729 Dated Sep. 25, 2013.
International Search Report for corresponding PCT Application Serial No. PCT/US2014/015382 dated May 6, 2014.
phys. org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.

* cited by examiner

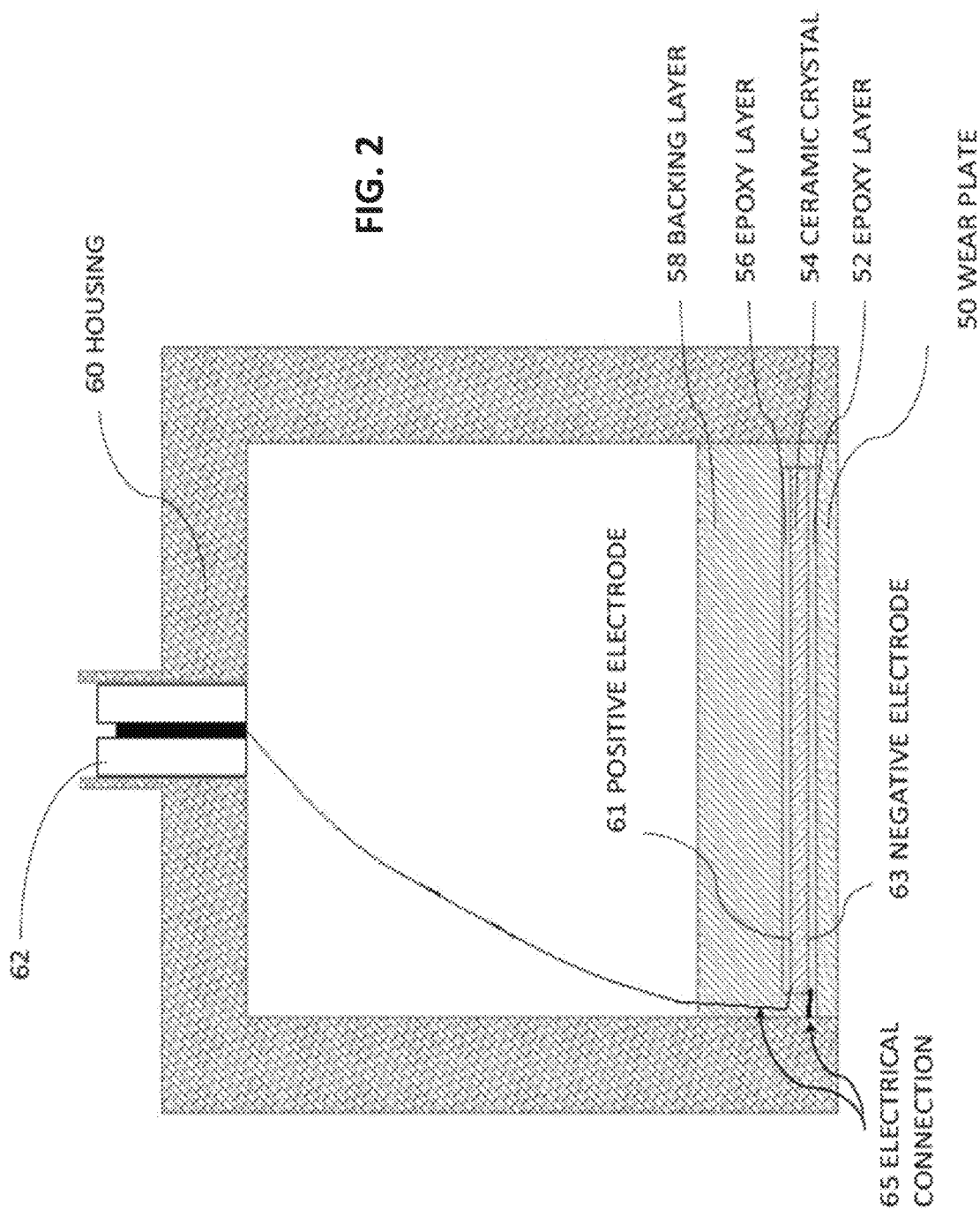

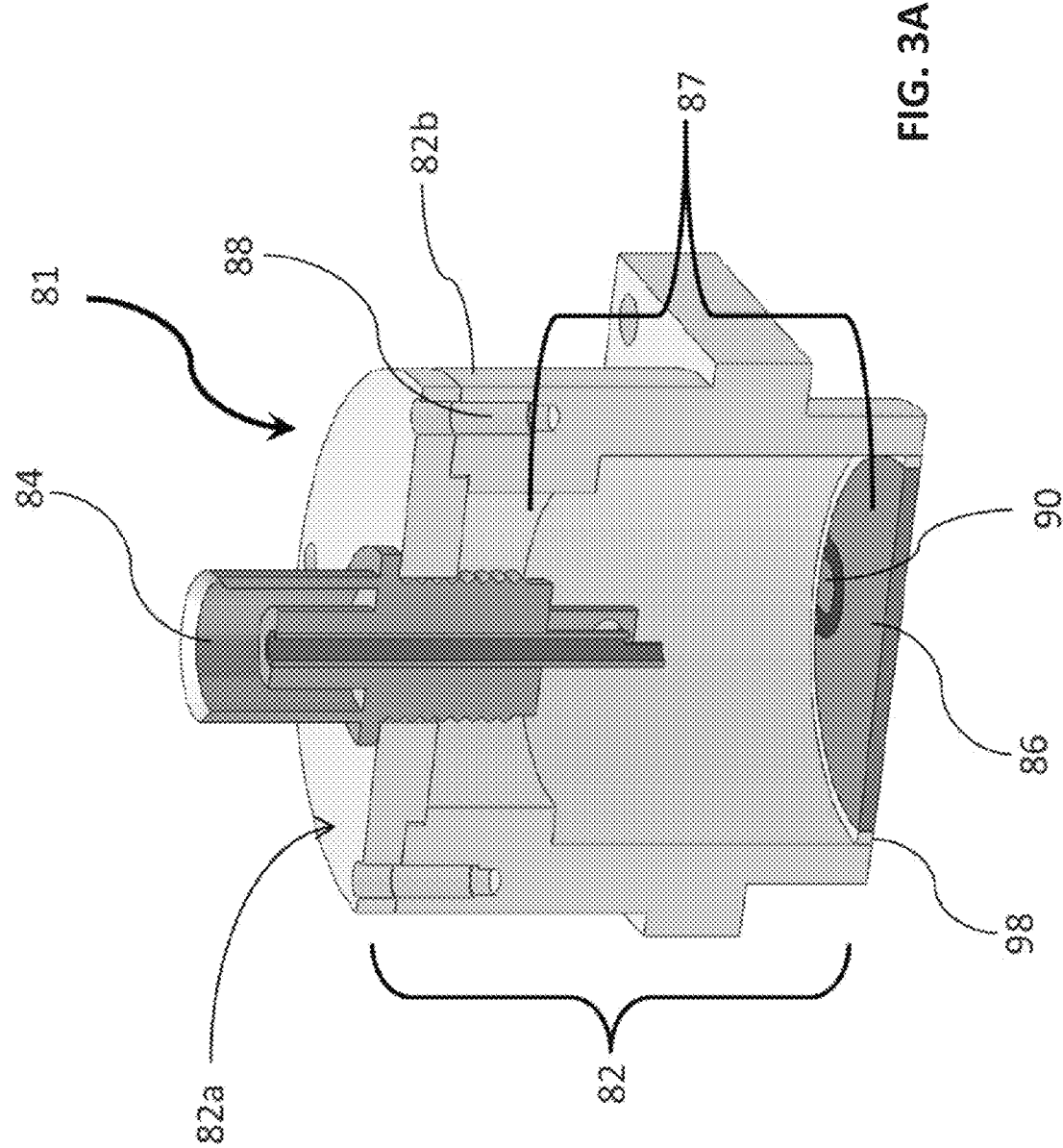

FLUID DYNAMIC SONIC SEPARATOR

This application claims the benefit of U.S. Provisional Patent Application No. 61/838,432, filed on Jun. 24, 2013, the content of which is hereby incorporated herein by reference in its entirety.

BACKGROUND

Acoustophoresis is the separation of particles using high intensity sound waves. It has long been known that high intensity standing waves of sound can exert forces on particles. A standing wave has a pressure profile which appears to "stand" still in time.

Standing waves are produced in acoustic resonators. Common examples of acoustic resonators include many musical wind instruments such as organ pipes, flutes, clarinets, and horns.

Efficient separation technologies for multi-component liquid streams that reduce the required energy, thereby promoting a sustainable environment, are needed. These separation technologies can be particularly useful in bioseparations applications and other separations involving suspended or dispersed particulates, liquids, or gases that are different in contrast factor from the host fluid.

BRIEF DESCRIPTION

The present disclosure relates to systems and devices for acoustophoresis on preferably a large scale. The devices use one or more unique ultrasonic transducers as described herein, or an array of such transducers. The transducer is driven at frequencies that produce multi-dimensional standing waves.

Disclosed in certain embodiments is an acoustophoresis device, comprising: one or more device inlets at a bottom end of the device, the bottom end having a first diameter for receiving fluid flow; a contoured wall above the inlet that narrows the fluid flow to a second diameter of a connecting duct; a flow chamber above the connecting duct, the flow chamber having: an inlet at a lower end for receiving the fluid flow, an outlet at a top end opposite the bottom end, at least one ultrasonic transducer located on a wall of the flow chamber, the ultrasonic transducer including a piezoelectric material driven by a voltage signal to create a multi-dimensional standing wave in the flow chamber, and a reflector located on a wall on the opposite side of the flow chamber from the at least one ultrasonic transducer; a first device outlet located at the bottom end of the device and separated from the device inlet by a longitudinal sidewall; and a second device outlet located at a top end of the device above the flow chamber outlet.

The device may include a plurality of device inlets spaced about the bottom end of the device, with the longitudinal sidewall being spaced apart from the contoured wall.

The piezoelectric material of the at least one ultrasonic transducer can have a rectangular shape. The reflector and/or the piezoelectric transducer can have a non-planar surface.

In particular embodiments, the bottom end of the device has a circular cross-section that narrows with decreasing elevation in the shape of a truncated cone, and the flow chamber also has a circular cross-section. In other embodiments, the bottom end of the device has a circular cross-section that narrows with decreasing elevation in the shape of a truncated cone, and the flow chamber has a rectangular cross-section.

The multi-dimensional standing wave generated by the transducer can result in an acoustic radiation force having an axial force component and a lateral force component that are of the same order of magnitude.

In embodiments, the transducer comprises: a housing having a first end, a second end, and an interior volume; and a crystal at the second end of the housing having an exposed exterior surface and an interior surface, the crystal being able to generate acoustic waves when driven by a voltage signal.

Sometimes, no backing layer is present within the housing, and an air gap is present in the interior volume between the crystal and a plate at the first end of the housing.

In other devices, the transducer further comprises a backing layer contacting the interior surface of the crystal, the backing layer being made of a substantially acoustically transparent material. The substantially acoustically transparent material can be balsa wood, cork, or foam. The substantially acoustically transparent material may have a thickness of up to 1 inch.

The flow chamber can further comprise a transparent window for viewing the interior of the flow chamber.

In particular embodiments, the device has a length L from the at least one device inlet to a bottom of the longitudinal sidewall, and a ratio of the length L to the first diameter is less than 1.

Also disclosed is a method for separating biological cells from a host fluid using the acoustophoresis device described in the present application. The mixture of biological cells and the host fluid is made to flow up through the device.

The mixture flows vertically upward and the cells flow vertically downward to a collection duct. This is after trapping of the cells at the nodes of the multidimentional standing wave, and the agglomeration of and collection of the cells in the multidimentional wave. This is followed by the cells eventually falling, due to gravity and their clumping together overcoming Stokes drag.

In certain embodiments, the cells separated are Chinese hamster ovary (CHO) cells, NS0 hybridoma cells, baby hamster kidney (BHK) cells, or human cells.

In other embodiments, the mixture of cells and host fluid has a Reynold's number of less than 1500 before reaching the flow chamber.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 2 is a cross-sectional diagram of a conventional ultrasonic transducer.

FIG. 3A is a cross-sectional diagram of an ultrasonic transducer of the present disclosure. An air gap is present within the transducer, and no backing layer or wear plate is present.

FIG. 6 shows the axial force for a single standing wave. The text at the top of the scale on the right is "×10$^{-11}$". FIG. 7 shows the lateral force for a single standing wave. The text at the top of the scale on the right is "×10$^{13}$". FIG. 8 shows the axial force with a multi-mode excitation. The text at the top of the scale on the right is "×10$^{-10}$". FIG. 9 shows the lateral force with a multi-mode excitation. The text at the top of the scale on the right is "×10$^{-11}$". For all figures, the horizontal axis is the location along the X-axis of FIG. 8 within the chamber, in inches, and the vertical axis is the location along the Y-axis of FIG. 8 within the chamber, in inches. The scale on the right of each figure is in Newtons.

FIG. 7 shows a simulation of the lateral forces on a particle in an acoustophoretic separator having a piezoelectric crystal producing a single standing wave.

FIG. 8 shows a simulation of the axial forces on a particle in an acoustophoretic separator having a piezoelectric crystal in a multi-mode excitation.

FIG. 9 shows a simulation of the lateral forces on a particle in an acoustophoretic separator a piezoelectric crystal in a multi-mode excitation.

DETAILED DESCRIPTION

Figure 1A:
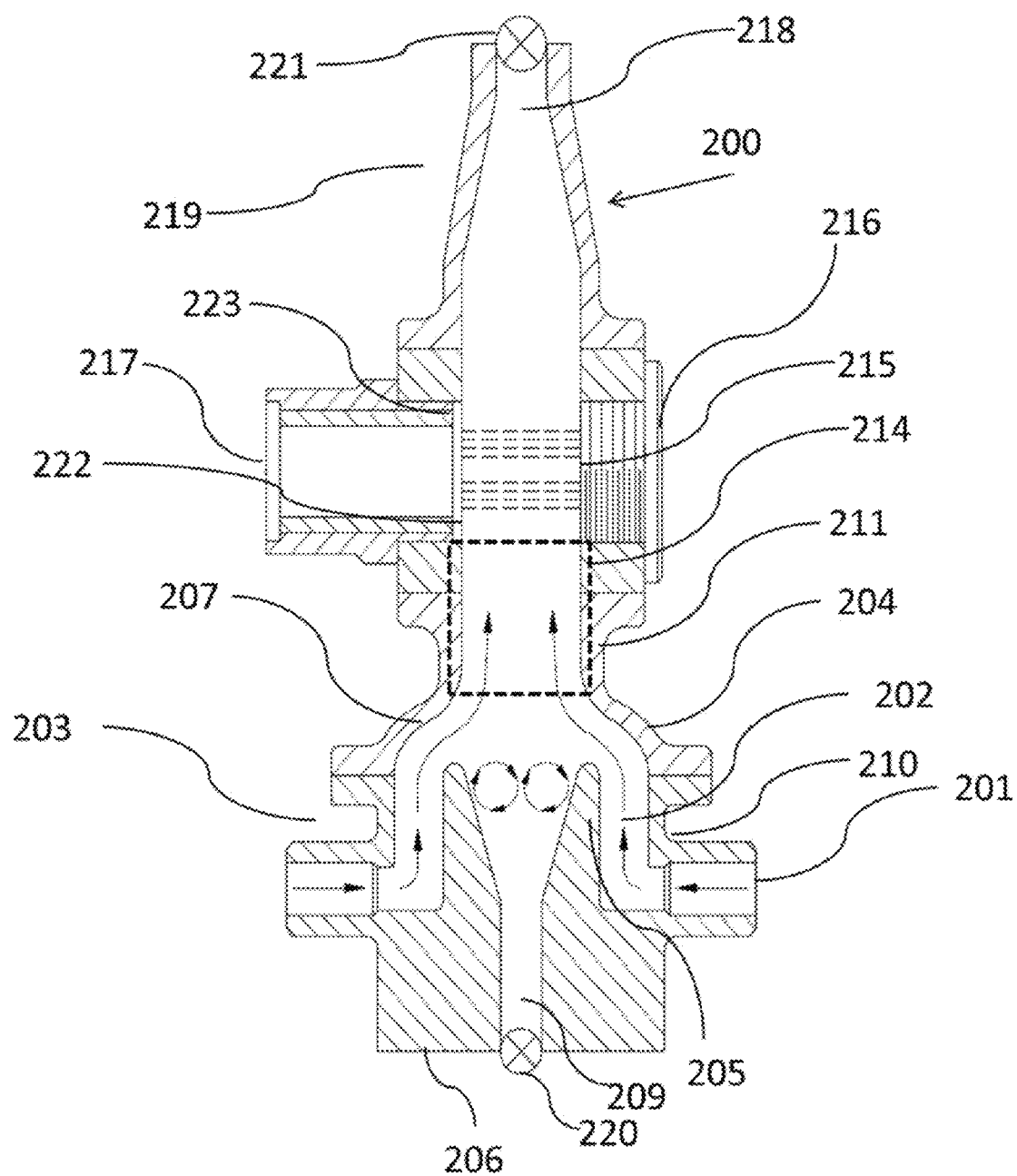
FIG. 1A is the cross-sectional view of an exemplary embodiment of a device of the present disclosure.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, along with any impurities that might result therefrom, and excludes other components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; an upwards flow is always against the gravity of the earth. Further, the terms "upper" and "lower" are relative to an absolute reference; i.e. an upper component is located at a higher elevation than a lower component relative to the earth's surface.

The present application refers to "the same order of magnitude." Two numbers are of the same order of magnitude if the quotient of the larger number divided by the smaller number is a value less than 10.

Efficient separation technologies for multi-component liquid streams that eliminate any waste and reduce the required energy, and therefore promote a sustainable environment, are needed. Large volume flow rate acoustophoretic phase separator technology using ultrasonic standing waves provides the benefit of having no consumables, no generated waste, and a low cost of energy. The technology is efficient at removal of particles of greatly varying sizes, including separation of micron and sub-micron sized particles. Examples of acoustic filters/collectors utilizing acoustophoresis can be found in commonly owned U.S. patent application Ser. Nos. 12/947,757; 13/085,299; 13/216,049; and 13/216,035, the entire contents of each being hereby fully incorporated by reference. Generally, an acoustophoretic system employs ultrasonic standing waves to trap (i.e. hold stationary) secondary phase particles, gases, or liquids that are suspended in a host fluid stream. The secondary phase can be continuously separated out of the host fluid as the mixture flows through the acoustophoretic system. The separation may also include tertiary and more phases or particles that are separated either at once or in sequence by the acoustophoresis device.

The platform technology described herein provides an innovative solution that includes a large volume flow rate acoustophoretic phase separator based on ultrasonic standing waves with the benefit of having no consumables, no generated waste, and a low cost of energy. Acoustophoresis is a low-power, no-pressure-drop, no-clog, solid-state approach to particle removal from fluid dispersions: i.e., it is used to achieve separations that are more typically performed with porous filters, but it has none of the disadvantages of filters. In particular, the present disclosure provides systems that operate at the macro-scale for separations in flowing systems with high flow rates. The acoustic resonator is designed to create a high intensity three dimensional ultrasonic standing wave that generates three dimensional pressure gradients and results in an acoustic radiation force that is larger than the combined effects of fluid drag and buoyancy or gravity, and is therefore able to trap (i.e., hold stationary) the suspended phase to allow more time for the acoustic wave to increase particle concentration, agglomeration and/or coalescence. The present systems have the ability to create ultrasonic standing wave fields that can trap particles in flow fields with a linear velocity ranging from 0.1 mm/sec to velocities exceeding 1 cm/s. This technology offers a green and sustainable alternative for separation of secondary phases with a significant reduction in cost of energy. Excellent particle separation efficiencies have been demonstrated for particle sizes as small as one micron.

This is an important distinction from previous approaches where particle trajectories were merely altered by the effect of the acoustic radiation force. The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and gravitational force, the particle is trapped within the acoustic standing wave field. The action of the acoustic forces on the trapped particles results in concentration, agglomeration and/or coalescence of particles and droplets. Additionally, secondary inter-particle forces, such as Bjerkness forces, aid in particle agglomeration. Particles which are denser than the host fluid are separated through enhanced gravitational settling.

It is also possible to drive multiple ultrasonic transducers with arbitrary phasing. In other words, the multiple transducers may work to separate materials in a fluid stream while being out of phase with each other. Alternatively, a single ultrasonic transducer that has been divided into an ordered array may also be operated such that some components of the array will be out of phase with other components of the array.

Efficient and economic particle separation processes can be useful in many areas of energy generation, e.g., producing water, hydro-fracking, and bio-fuels, e.g, harvesting and dewatering. Most of the successful work previously done using acoustophoresis particle separation has been conducted at the MEMS scale in the biomedical area. Such work is important for research, but has limited use in the many industrial processes requiring high flow rates and continuous operation.

Acoustophoretic separation can also be used to aid such applications as advanced bio-refining technology to convert low-cost readily available non-food biomass (e.g. municipal solid waste and sewage sludge) into a wide array of chemicals and secondary alcohols that can then be further refined into renewable gasoline, jet fuel, or diesel. A water treatment technology is used to de-water the fermentation broth and isolate valuable organic salts for further processing into fuels. The dewatering process is currently done through an expensive and inefficient ultra-filtration method that suffers from frequent fouling of the membranes, a relatively low concentration factor, and a high capital and operating expense. Acoustophoretic separation can filter out particles with an incoming particle size distribution that spans more than three orders of magnitude, namely from 600 microns to 0.3 microns, allowing improvements in the concentration of the separated broth with a lower capital and operational expense.

One specific application for the acoustophoresis device is in the processing of bioreactor materials. In a fed batch bioreactor, it is important at the end of the production cycle to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over the current filtration processes (depth filtration, tangential flow filtration, centrifugation), which show limited efficiencies at high cell densities, so that the loss of the expressed materials in the filter beds themselves can be up to 5% of the materials produced by the bioreactor. The use of mammalian cell culture include Chinese hamster ovary (CHO), NS0 hybridoma cells, baby hamster kidney (BHK) cells, and human cells has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the fed batch bioreactor.

Another type of bioreactor, a perfusion reactor, uses continuous expression of the target protein or monoclonal antibodies from the CHO cells. This enables a much smaller footprint in a faster production cycle. The use of acoustophoresis to hold the CHO cells in a fluid stream as they are producing/expressing the proteins is a very efficient and closed loop way of production. It also allows for a maximum production efficiency of the proteins and monoclonal antibodies in that none of the materials are lost in a filter bed.

In the fed batch bioreactor process, the acoustophoresis device uses singular or multiple standing waves to trap the cells and cell debris. The cells and cell debris, having a positive contrast factor, move to the nodes (as opposed to the anti-nodes) of the standing wave. As the cells and cell debris agglomerate at the nodes of the standing wave, there is also a physical scrubbing of the fluid stream that occurs whereby more cells are trapped as they come in contact with the cells that are already held within the standing wave. When the cells in the standing wave agglomerate to the extent where the mass is no longer able to be held by the acoustic wave, the aggregated cells and cell debris that have been trapped fall out of the fluid stream through gravity, and can be collected separately. To aid this gravitational settling of the cells and cell debris, the standing wave may be interrupted to allow all of the cells to fall out of the fluid stream that is being filtered from the fed batch bioreactor.

Desirably, the ultrasonic transducers generate a three-dimensional standing wave in the fluid that exerts a lateral force on the suspended particles/secondary fluid to accompany the axial force so as to increase the particle trapping capabilities of a acoustophoretic system. Typical results published in literature state that the lateral force is two orders of magnitude smaller than the axial force. In contrast, the technology disclosed in this application provides for a lateral force to be of the same order of magnitude as the axial force.

The present disclosure relates to the use of an acoustic standing wave generated by an ultrasonic transducer or transducers to separate components from a host fluid, where the components are denser than the host fluid. Excitation frequencies typically in the range from hundreds of kHz to 10 s of MHz are applied to a mixture by transducer. Particles in the incoming mixture are trapped in standing waves at the pressure nodes or antinodes where they agglomerate, aggregate, clump, or coalesce, and sink to the bottom collector and are discharged via an effluent collection outlet located below the flow path.

Depending on the contrast factor of the particle being separated, the agglomerated particles will collect at either the nodes or antinodes of the ultrasonic radiation. In a typical experiment, the transducer system is operated at a voltage such that the particles are trapped in the ultrasonic standing wave, i.e., remain in a stationary position. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. It therefore must be larger than the combined effect of fluid drag force and gravitational force. For small particles or emulsions the drag force FD can be expressed as:

$$\vec{F}_D = 4\pi\mu_f R_p (\vec{U}_f - \vec{U}_p) \left[ \frac{1 + \frac{3}{2}\hat{\mu}}{1 + \hat{\mu}} \right],$$

where $U_f$ and $U_p$ are the fluid and particle velocity, $R_p$ is the particle radius, $\mu_f$ and $\mu_p$ are the dynamic viscosity of the fluid and particle, and $\hat{\mu}=\mu_p/\mu_f$ is the ratio of dynamic viscosities. The buoyancy force $F_B$ is expressed as:

$$F_B = \frac{4}{3}\pi R_p^3 (\rho_f - \rho_p).$$

For a particle to be trapped in the ultrasonic standing wave, the force balance on the particle must be zero, and therefore an expression for lateral acoustic radiation force $F_{LRF}$ can be found, which is given by:

$$F_{LRF} = F_D + F_B.$$

For a particle of known size and material property, and for a given flow rate, this equation can be used to estimate the magnitude of the lateral acoustic radiation force.

The theoretical model that is used to calculate the acoustic radiation force is the formulation developed by Gor'kov. The primary acoustic radiation force $F_A$ is defined as a function of a field potential U, $F_A = -\nabla(U)$, where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda\sigma^2},$$

$$f_2 = \frac{2(\Lambda - 1)}{2\Lambda + 1},$$

where p is the acoustic pressure, u is the fluid particle velocity, $\Lambda$ is the ratio of particle density $\rho_p$ to fluid density $\rho_f$, $\sigma$ is the ratio of particle sound speed $c_p$ to fluid sound speed $C_f$, and $V_o$ is the volume of the particle. For a one dimensional standing wave, where the acoustic pressure is expressed as $$p = A \cos(kx)\cos(\omega t),$$

where A is the acoustic pressure amplitude, k is the wavenumber, and w is the angular frequency. In this case, there is only the axial component of the acoustic radiation force $F_{ARF}$, which is found to be $$F_{ARF} = V_0 k X \frac{A^2}{4\rho_f c_f^2} \sin(2kx),$$

where X is the contrast factor given by $$X = \left( \frac{5\Lambda - 2}{1 + 2\Lambda} - \frac{1}{\sigma^2 \Lambda} \right).$$

Particles with a positive contrast factor will be driven to the pressure nodal planes, and particles with a negative contrast factor will be driven to the pressure anti-nodal planes.

Gor'kov's theory is limited to particle sizes that are small with respect to the wavelength of the sound fields in the fluid and the particle, and it also does not take into account the effect of viscosity of the fluid and the particle on the radiation force. Additional numerical models have been developed for the calculation of the acoustic radiation force for a particle without any restriction as to particle size relative to wavelength. These models also include the effect of fluid and particle viscosity, and therefore are a more accurate calculation of the acoustic radiation force. The models that were implemented are based on the theoretical work of Yurii Ilinskii and Evgenia Zabolotskaya.

In the present disclosure, a 3-D acoustic standing wave is generated by causing the ultrasonic transducer to generate multiple waves. The types of waves generated in the plate can be characterized as composite waves, with displacement profiles that are similar to leaky symmetric (also referred to as compressional or extensional) Lamb waves. The piezoelectric nature of the plate typically results in the excitation of composite wave motion similar to that of symmetric Lamb waves. The waves are leaky because they radiate into the water layer, which result in the generation of the acoustic standing waves in the water layer. Symmetric Lamb waves have displacement profiles that are symmetric with respect to the neutral axis of the plate as opposed to a "piston" fashion. Symmetric Lamb waves operation of the piezoelectric element in the ultrasonic transducer causes multiple standing waves to be generated in a 3-D space. This is opposed to the action of the piezoelectric crystal in the ultrasonic transducer acting in a "piston" fashion where a single standing wave is produced. Through the use of a 3-D multi-standing wave, macro-scale trapping of particles or a secondary fluid may be accomplished. This allows for high volumes of fluid to be treated and the particles or secondary fluid to be separated from the first fluid.

The piezoelectric crystal in the ultrasonic transducer may be directly interfaced with the fluid stream or may have a protective layer or matching layer over the surface of the piezoelectric crystal that is interfaced with the fluid stream. The protective layer may be a coating, such as a polyurethane or epoxy. The protective layer may also be plated onto the surface of the piezoelectric crystal that is interfaced with the fluid stream. The plated layer may be added to the surface of the piezoelectric crystal through either electrolytic or electroless plating. The plating material may be nickel, chrome, copper, indium or combination of layers of these materials. Also, the secondary material or matching layer may be adhered to the surface of the piezoelectric crystal such that the matching layer is now interfaced with the fluid stream. The matching layer may be a material such as a stainless steel that is adhered to the piezoelectric crystal through the use of a two-part epoxy system.

Figure 1B:
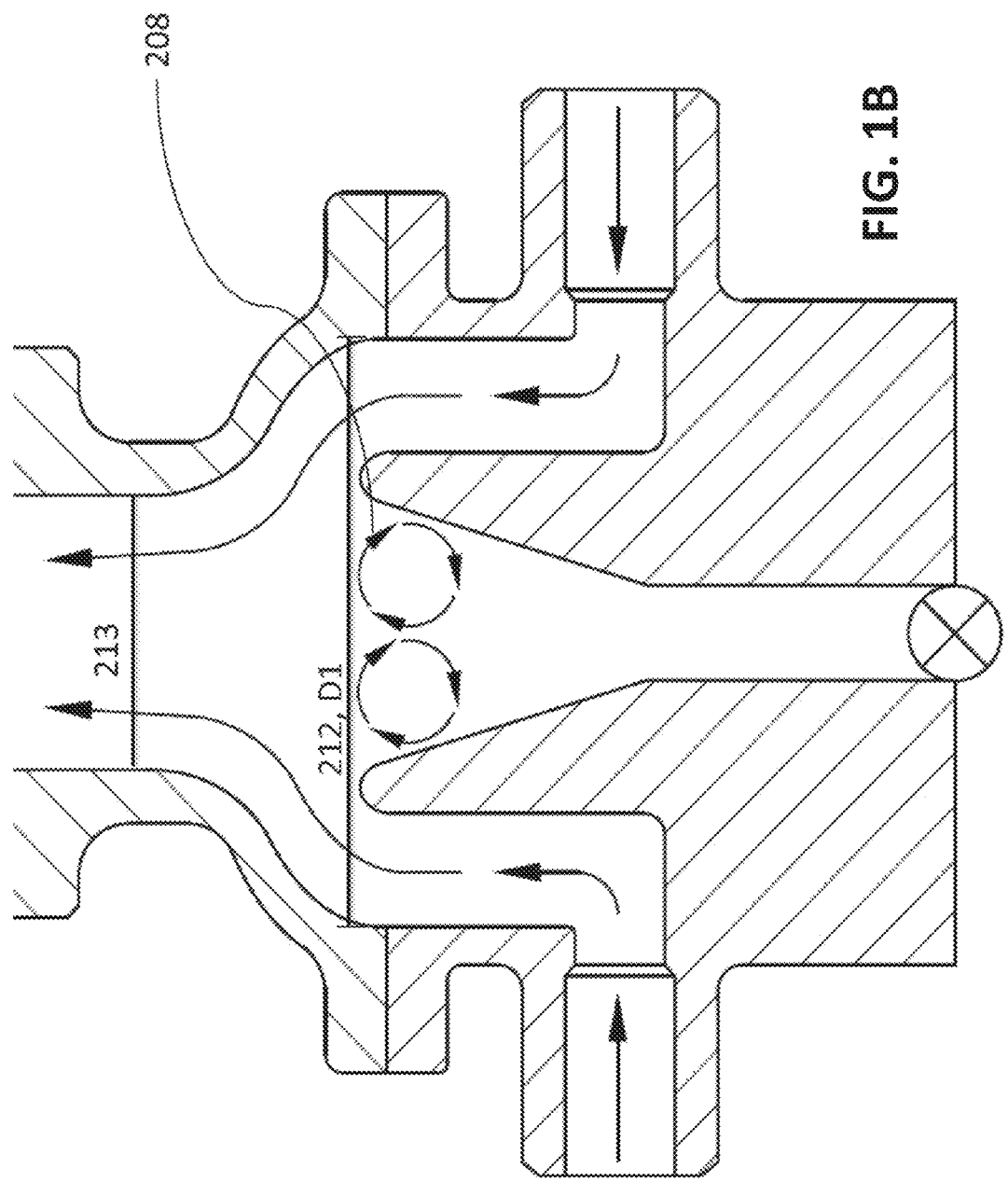
FIG. 1B is an expanded view of the bottom portion of the device shown in FIG. 1A.

FIGS. 1A-B show an acoustophoresis device of the present disclosure. Generally, the acoustophoresis device uses the ultrasonic transducer to separate suspended particles/droplets in a fluid stream into ordered, coalesced and agglomerated particles trapped in a standing wave of the acoustophoresis device. The flow of the fluid stream is from the lower end upward (i.e. against gravity). The fluid stream can enter the device through one of many inlets that surround a central collection outlet for the agglomerated and separated particulates. The fluid stream flows into the acoustophoresis separation device from a pump through the inlet. The agglomerated and coalesced particles clump together and fall into the central collection outlet while the acoustophoresis device is in continuous operation. This collection and dropping out of particles and/or agglomeration and buoyancy of secondary fluids is a continuous process that is accomplished without shutting off the power of the unit. The device is shown here in an orientation where the flow direction is upwards, which allows for separating more-dense particles from the host fluid.

The trapping in this embodiment of the acoustophoretic device allows for a continuous process of trapping, agglomerating and shedding of particles due to the trapping characteristics of the multidimensional standing wave. A single, planar acoustic standing wave will trap and hold particles such that the device will need to be shut off in order for the trapped particles to fall out of the acoustic standing planar wave. The multidimensional standing wave will also "tumble" where the multidimensional trapping lines will appear to change location in space in a tumbling fashion. This is advantageous in the trapping of the particles due to the fact that the tumbling action allows for continuous shedding of the agglomerated or clumped cells and thus continuous concentration of the cells during continuous operation of the acoustophoresis device (i.e. there is not a need to shut off the power and dissipate the standing wave, such as in a single, planar standing wave system, for the particles to fall out of the standing wave and be concentrated in a concentration area).

The initial fluid stream is made up of a host fluid (e.g. water) and a suspended phase (e.g. cells/droplets/particles). The fluid stream enters the device 200 through one or more device inlets 201 into an annular plenum 202 at a lower end 203 of the device. The lower end 203 includes an outer sidewall 204 and an inner longitudinal sidewall 205. An end wall 206 is also visible, from which the longitudinal sidewall extends. The term "annular," as used herein, only designates the area or volume between the outer sidewall and the inner longitudinal sidewall, and should not be construed as requiring the first end of the device to have a circular cross-section. However, in contemplated embodiments the first end of the device has a circular cross-section. The construction of the plenum guides the fluid stream flow upwards in the direction of the centerline, i.e. with little to no radial or circumferential motion component. This helps to create laminar/plug flow later downstream. One device inlet 201 is shown here, with one other inlet being shown. It is contemplated that any number of inlets may be provided as desired. In particular embodiments, two inlets are used. The inlets are radially oriented.

A contoured nozzle wall 207 reduces the outer diameter of the flow path, which generates higher velocities near the wall and reduces turbulence, producing near plug flow as the fluid velocity profile develops and the fluid passes through the connecting duct and into a flow/separation chamber. The contoured wall also adds a radial motion component to the suspended particles, moving the particles closer to the centerline of the device and generating more collisions with falling, heavy agglomerated particles. This radial motion will allow for optimum scrubbing of the particles from the fluid in the connecting duct prior to reaching the separation chamber. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension. The contoured nozzle wall further directs the fluid in a manner that generates large scale vortices 208 at the entrance of the bottom device outlet 209 to also enhance particle collection. Generally, the flow area of the device is designed to be continually decreasing from the device inlets to the separation chamber to assure low turbulence and eddy formation for better particle separation, agglomeration, and collection. Put another way, the contoured wall 207 has a wide end 210 and a narrow end 211. The bottom end of the device/the wide end of the nozzle wall has a first diameter 212, and the narrow end of the nozzle wall has a second diameter 213. The second diameter is less than the first diameter. The connecting duct 214 is above the nozzle wall and connects to the inlet of the flow chamber 215.

The flow chamber 215 is above the connecting duct 214 and has an inlet 222 at a lower end, and an outlet 223 at an upper end opposite the lower end. At least one ultrasonic transducer 216 is present on a wall, and a reflector 217 is located on a wall opposite the transducer. Multiple transducers can be used, as desired. In use, standing waves are created between the transducer 216 and reflector 217. These standing waves can be used to agglomerate particles, and this orientation is used to agglomerate particles that are denser than the host fluid (e.g. some cells in water). Fluid, containing residual particles, then exits through the flow chamber outlet and through a second device outlet 218 located at an upper end 219 of the device opposite the lower end 203 of the device. It is contemplated that in particular embodiments, the flow chamber has a circular cross-section and a rectangular cross-section in others. The flow chamber inlet and outlets have a circular cross-section for interfacing with the other components of the device.

As the denser particles agglomerate, they eventually overcome the combined effect of the fluid flow drag forces and acoustic radiation force, and their force due to gravity is sufficient to cause the particles to fall downwards. In this regard, a lower device outlet or collection duct 209 is present at the bottom/lower end of the device 203, and is surrounded by the longitudinal sidewall 205, or put another way is separated from the device inlets 201 by the longitudinal sidewall 205, or put yet another way the lower device outlet is a hole in the end wall 206. The collection duct 209 further has a truncated conical shape with a circular cross-sectional area that narrows with decreasing elevation. The agglomerated denser particles exit the device through the lower device outlet 209. The lower device outlet and the upper device outlet are on opposite ends of the device.

Further, control valves 220 and 221 may be located at the bottom outlet 209 and the top outlet 218, respectively. These valves can be used to adjust flow rates and flow patterns in the device. Bleeding more through the bottom outlet 209 will result in a more severe velocity profile, having a lower velocity in the center and higher velocity at the boundaries in the connecting duct 214, and a consequently longer length for scrubbing by the sinking, agglomerated particles. The collection vortices 208 at the beginning of the bottom outlet 209 will also become stronger. It should further be noted that the flow rate through the upper control valve 221 and outlet 218 will be stronger than it will be through the lower control valve 220 and outlet 209 when the device is operating properly.

It should be noted that the denser particles formed in the flow chamber 215 subsequently pass through the connecting duct 214. This causes the incoming fluid stream flow from the device inlets 201 to flow past the falling agglomerated particles due to the inward radial motion imparted by the contoured wall 207. This allows the falling particles to also trap smaller particles in the incoming flow, increasing scrubbing effectiveness. The length of the connecting duct and the contoured nozzle wall thus increase scrubbing effectiveness. Especially high effectiveness is found for particles with a size of 0.1 microns to 10 microns, where efficiency is very low for conventional methods. As noted here, the distance from the device inlets 201 to the bottom of the longitudinal sidewall 205 is denoted as length, L. The first diameter is marked as D1 (reference numeral 212). This length-to-diameter ratio here (i.e. L/D1) is less than 1.

The design here results in low flow turbulence at the flow chamber inlet, a scrubbing length before (i.e. upstream of) the flow chamber to enhance particle agglomeration and/or coalescence before acoustic separation, and the use of the collection vortices to aid particle removal upstream of the flow chamber. This is accomplished without the use of flow strengtheners, which will detract from particle collection.

The ultrasonic transducer(s) are arranged to cover the entire cross-section of the fluid stream flowpath. In certain embodiments, the flow chamber has a square cross section of 6 inches×6 inches which operates at flow rates of up to 3 gallons per minute (GPM), or a linear velocity of 8 mm/sec. The transducer can be a PZT-8 (Lead Zirconate Titanate) transducer with a 1-inch diameter and a nominal 2 MHz resonance frequency. Each transducer consumes about 28 W of power for droplet trapping at a flow rate of 3 GPM. This translates in an energy cost of 0.25 kW hr/m$^3$. This is an indication of the very low cost of energy of this technology. Desirably, when multiple transducers are present, each transducer is powered and controlled by its own amplifier. This device shifts the particle size distribution in the host fluid through agglomeration of smaller particles/droplets into larger particles/droplets.

FIG. 2 is a cross-sectional diagram of a conventional ultrasonic transducer. This transducer has a wear plate/protective layer 50 at a second end, epoxy layer 52, piezoelectric material 54 (made of, e.g. PZT), an epoxy layer 56, and a backing layer 58. The epoxy layer 56 attaches backing layer 58 to the crystal 54. The entire assembly is contained in a housing 60 which may be made out of, for example, aluminum. A connector 62 provides connection for wires to pass through the housing and connect to leads (not shown) which attach to the piezoelectric material 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates, and face in the direction in which the wave is generated. The piezoelectric material can be, for example, a ceramic crystal.

FIG. 3A is a cross-sectional view of an ultrasonic transducer 81 of the present disclosure, which can be used with the acoustophoretic separator of FIG. 1A. Transducer 81 has an aluminum housing 82. A PZT crystal 86 defines the second end of the transducer, and is exposed from the exterior of the housing. The crystal is supported on its perimeter by a small elastic layer 98, e.g. silicone or similar material, located between the crystal and the housing. Put another way, no wear layer is present. The housing may also be composed of a more electrically conductive material, such as steel. The housing may also be grounded to the negative side of the transducer.

Figure 3B:
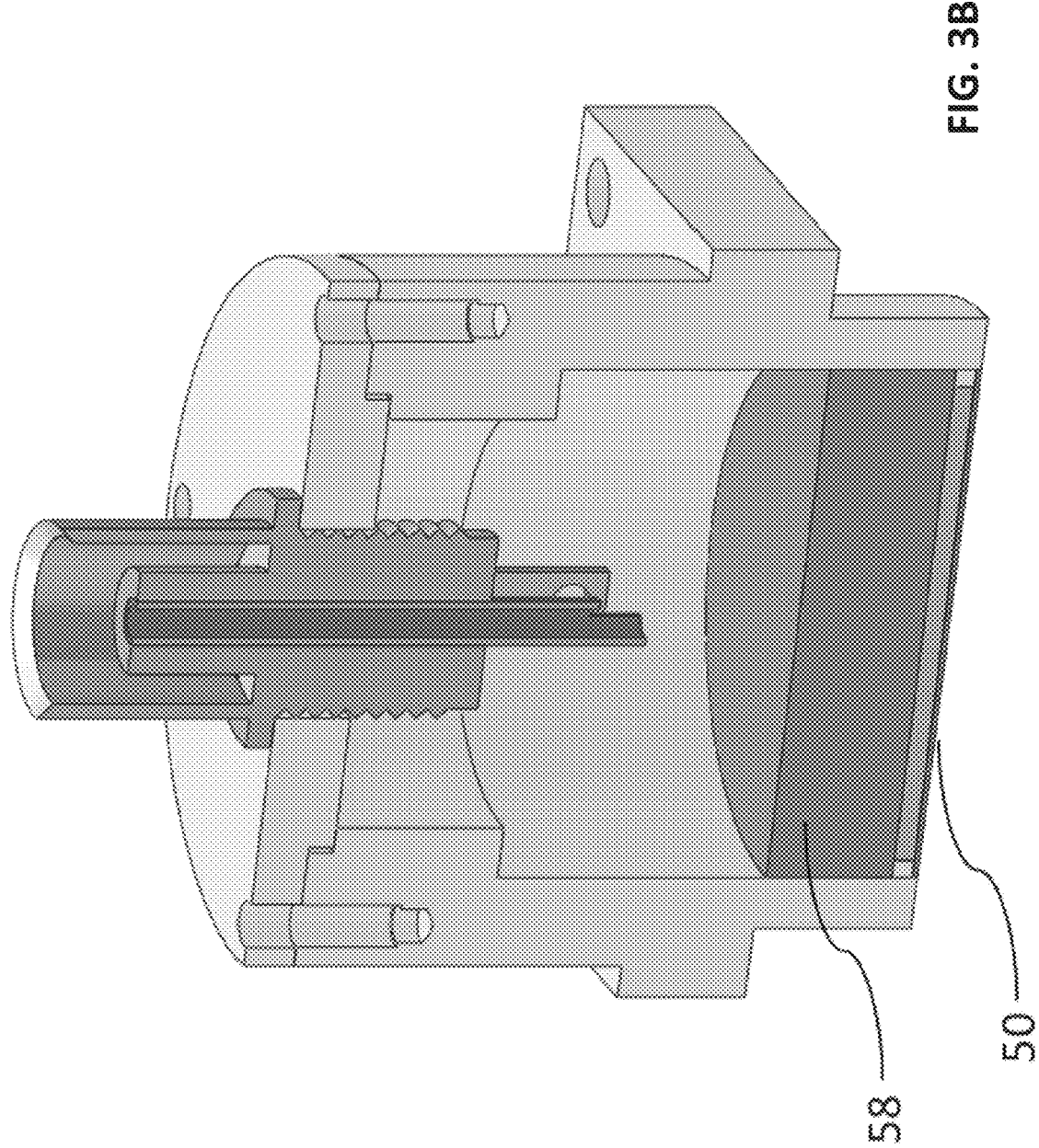
FIG. 3B is a cross-sectional diagram of an ultrasonic transducer of the present disclosure. An air gap is present within the transducer, and a backing layer and wear plate are also present.

Screws (not shown) attach an aluminum plate 82a of the housing at a first end to the body 82b of the housing via threads 88. The plate at the first end includes a connector 84 to pass power to the PZT crystal 86. The second and first surfaces of the PZT crystal 86 are each connected to an electrode (positive and negative), such as silver or nickel. A wrap-around electrode tab 90 connects to the second electrode and is isolated from the first electrode. Electrical power is provided to the PZT crystal 86 through the electrodes on the crystal, with the wrap-around tab 90 being the ground connection point. Note that the crystal 86 has no backing layer or epoxy layer as is present in FIG. 2. Put another way, there is an air gap 87 in the transducer between the aluminum plate 82a at the first end and the crystal 86 (i.e. the air gap is completely empty). A minimal backing 58 and/or wear plate 50 may be provided in some embodiments, as seen in FIG. 3B.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes with a high Q-factor. The vibrating ceramic crystal/disk is directly exposed to the fluid flowing through the flow chamber.

Removing the backing (e.g. making the crystal air backed) also permits the ceramic crystal/piezoelectric material to vibrate higher order modes of vibration (e.g. higher order modal displacement) with little damping. In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines. In the present disclosure, the transducers are driven so that the piezoelectric crystal vibrates in higher order modes of the general formula (m, n), where m and n are independently 1 or greater. In practice, the transducers of the present disclosure will vibrate at higher orders than (1,2).

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. In another embodiment, the backing may be a lattice work that follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface/protective layer to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylxyene) (e.g. Parylene) or other polymer. Organic and biocompatible coatings such as silicone or polyurethane are also contemplated for use as a wear surface.

2D axisymmetric models were developed to calculate the trapping forces for circular transducers. The models were used to predict acoustic trapping forces on particles, which can then be used to predict particle trajectories in combination with the action of fluid drag and gravitational forces. The models clearly show that it is possible to generate lateral acoustic trapping forces necessary to trap particles and overcome the effects of the gravitational force and fluid drag. The models also show that circular transducers do not provide for large trapping forces across the entire volume of the standing wave created by the transducer, indicating that circular transducers only yield high trapping forces near the center of the ultrasonic standing wave generated by the transducer, but provide much smaller trapping forces toward the edges of the standing wave. This further indicates that circular transducers only provide limited trapping for a small section of the fluid flow that would flow across the standing wave of the circular transducer, and no trapping near the edges of the standing wave.

Square transducers likely provide better separation efficiencies than round transducers, explained by the fact that square transducers provide better coverage of the flow channel with acoustic trapping forces, and that round transducers only provide strong trapping forces along the centerline of the standing wave.

The size, shape, and thickness of the transducer determine the transducer displacement at different frequencies of excitation, which in turn affects separation efficiency. Typically, the transducer is operated at frequencies near the thickness resonance frequency (half wavelength). Gradients in transducer displacement typically result in more places for particles to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 4:
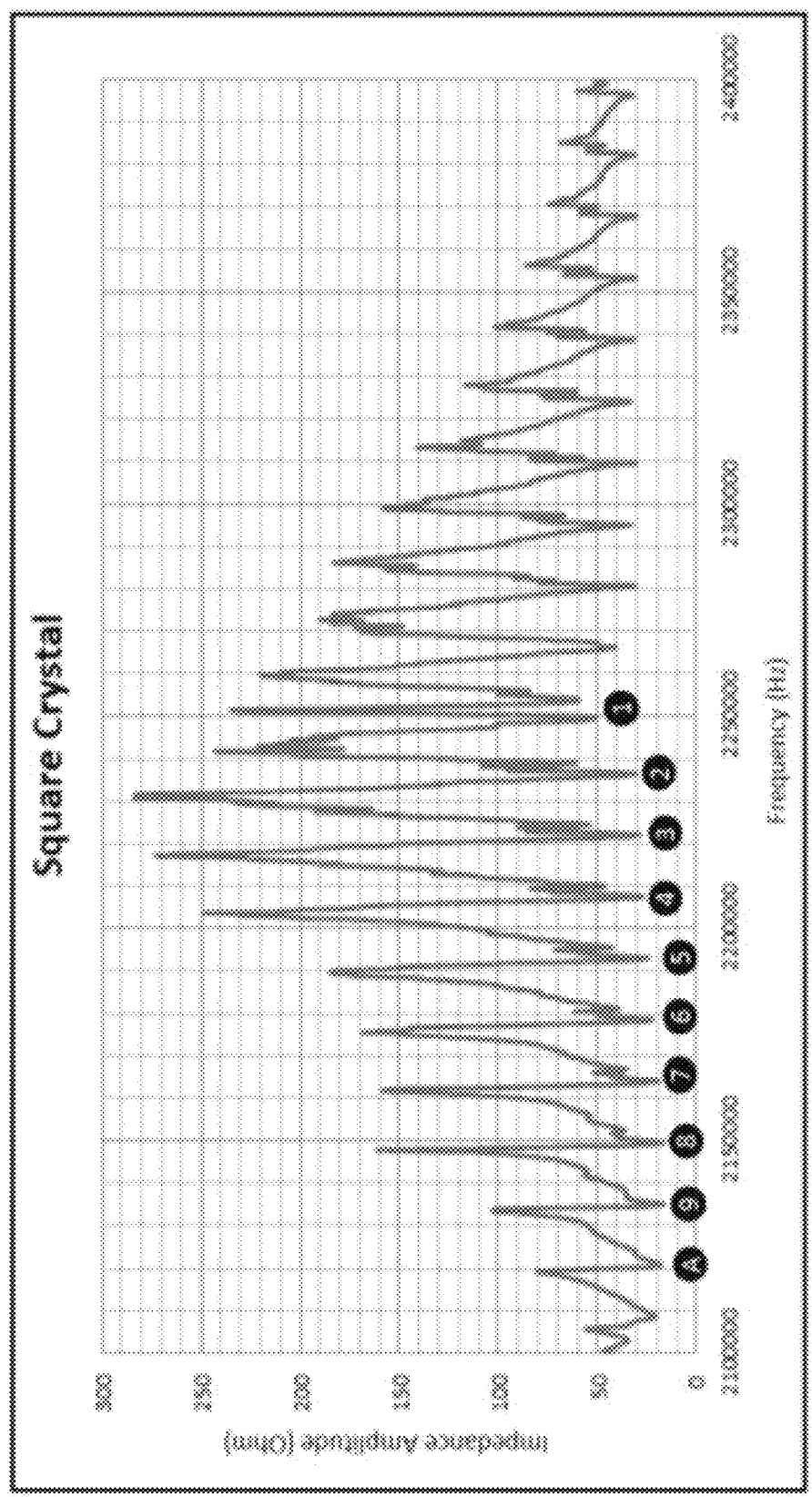
FIG. 4 is a graph of electrical impedance amplitude versus frequency as a square transducer is driven at different frequencies.

FIG. 4 shows the measured electrical impedance amplitude of the transducer as a function of frequency in the vicinity of the 2.2 MHz transducer resonance. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped particles/droplets, the displacement has a single maximum in the middle of the electrode and minima near the transducer edges. At another excitation frequency, the transducer profile has multiple maxima leading to multiple trapped lines of particles/droplets. Higher order transducer displacement patterns result in higher trapping forces and multiple stable trapping lines for the captured particles/droplets.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five nodal trapping lines are observed. Different displacement profiles of the transducer can produce different (more) trapping lines of the standing waves, with more gradients in displacement profile generally creating higher trapping forces and more trapping lines.

Arrays of closely spaced transducers represent alternate potential embodiments of the technology. Transducer size, shape, number, and location can be varied as desired to generate desired three-dimensional acoustic standing waves.

Figure 5:
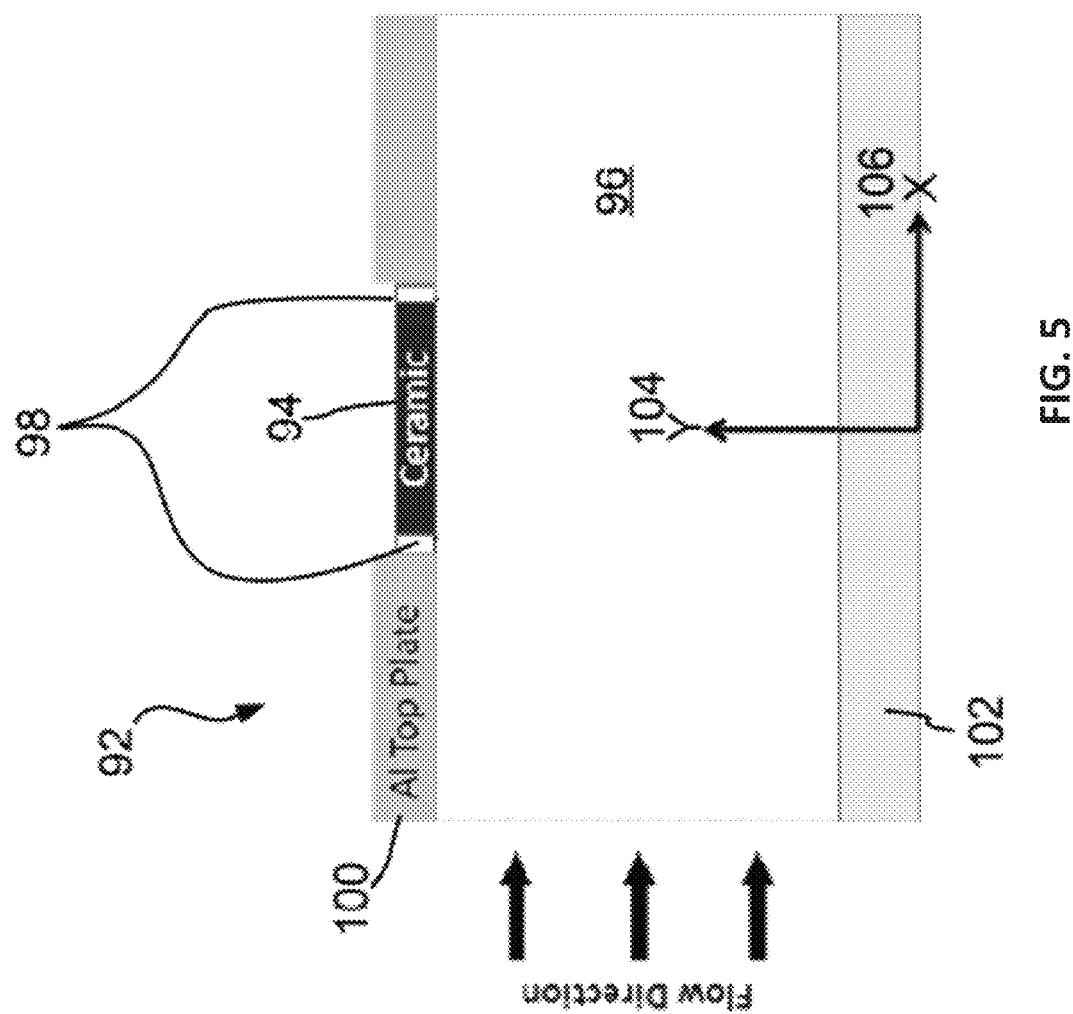
FIG. 5 is a computer model of an acoustophoretic separator simulated to generate FIGS. 6-9.

FIG. 5 is a computer model of an acoustophoretic separator 92 simulated to produce FIGS. 6-9. The piezo ceramic crystal 94 is in direct contact with the fluid in the water channel 96. A layer of silicon 98 is between the crystal 94 and the aluminum top plate 100. A reflector 102 reflects the waves to create standing waves. The reflector is made of a high acoustic impedance material such as steel or tungsten, providing good reflection. For reference, the Y-axis 104 will be referred to as the axial direction. The X-axis 106 will be referred to as the radial or lateral direction. The acoustic pressure and velocity models were calculated in COMSOL including piezo-electric models of the PZT transducer, linear elastic models of the surrounding structure (e.g. reflector plate and walls), and a linear acoustic model of the waves in the water column. The acoustic pressure and velocity was exported as data to MATLAB. The radiation force acting on a suspended particle was calculated in MATLAB using Gor'kov's formulation. The particle and fluid material properties, such as density, speed of sound, and particle size, are entered into the program, and used to determine the monopole and dipole scattering contributions. The acoustic radiation force is determined by performing a gradient operation on the field potential U, which is a function of the volume of the particle and the time averaged potential and kinetic energy of the acoustic field.

Figures 6, 7:
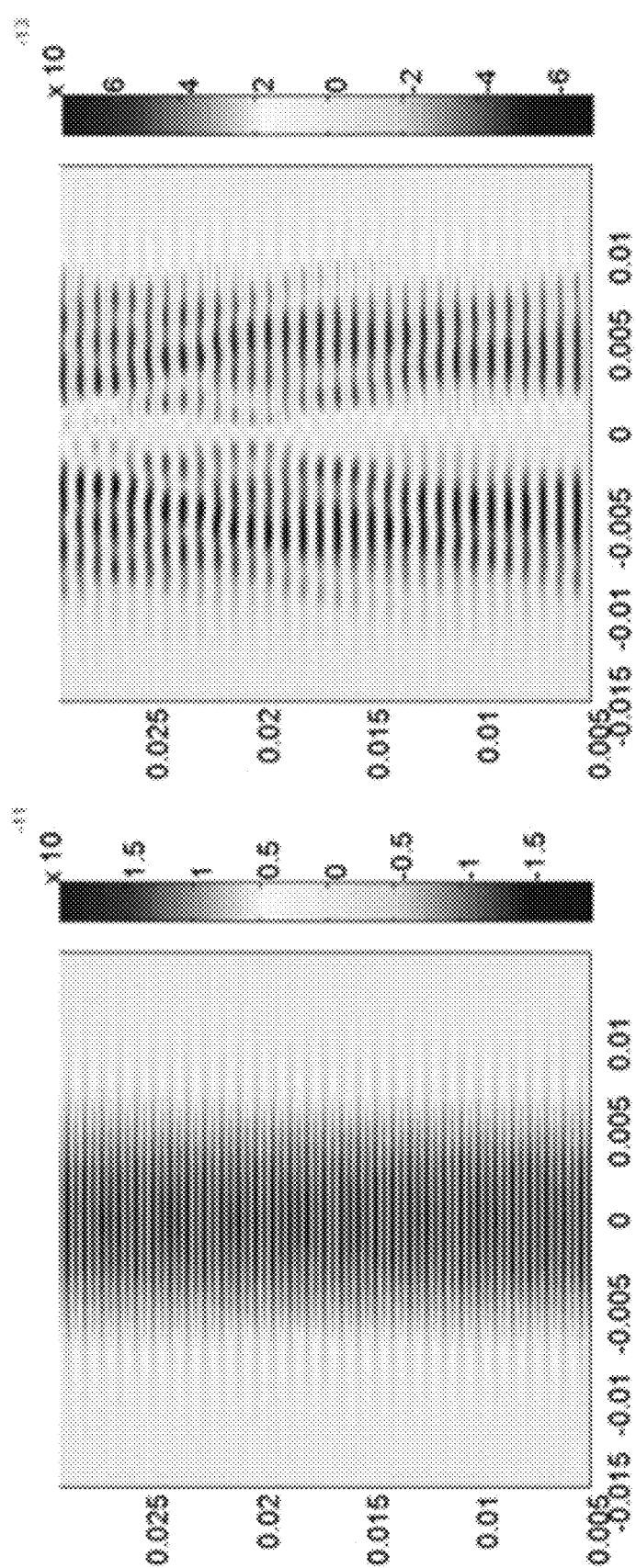
FIGS. 6-9 show simulations of the forces on a particle in an acoustophoretic separator.
Figures 8, 9:
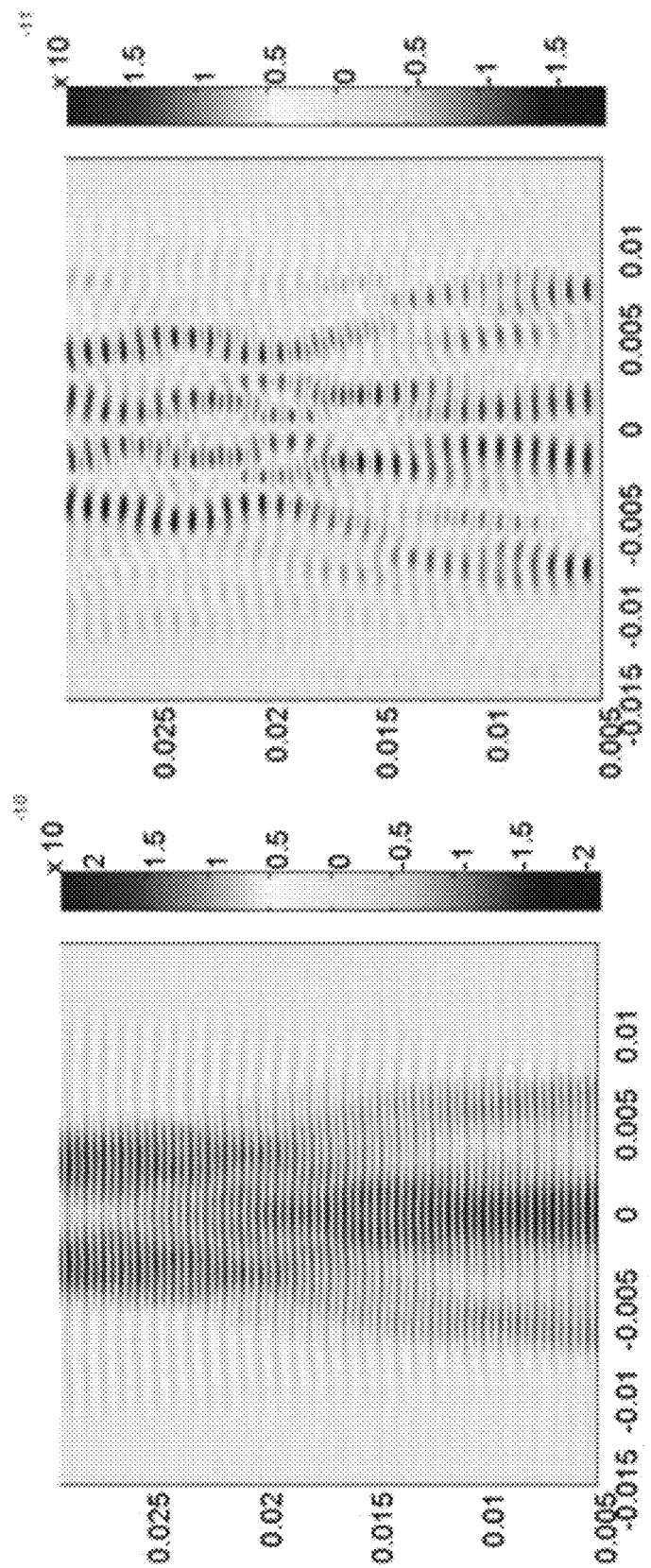

FIGS. 6-9 show simulations of the difference in trapping pressure gradients between a single acoustic wave and a multimode acoustic wave. FIG. 6 shows the axial force associated with a single standing acoustic wave. FIG. 7 shows the lateral force due to a single standing acoustic wave. FIG. 8 and FIG. 9 show the axial force and lateral force, respectively, in a multi-mode (higher order vibration modes having multiple nodes) piezoelectric crystal excitation where multiple standing waves are formed. The electrical input is the same as the single mode of FIG. 6 and FIG. 7, but the trapping force (lateral force) is 70 times greater (note the scale to the right in FIG. 6 compared to FIG. 9). The figures were generated by a computer modeling simulation of a 1 MHz piezo-electric transducer driven by 10 V AC potted in an aluminum top plate in an open water channel terminated by a steel reflector (see FIG. 5). The field in FIG. 6 and FIG. 7 is 960 kHz with a peak pressure of 400 kPa. The field in FIG. 8 and FIG. 9 is 961 kHz with a peak pressure of 1400 kPa. In addition to higher forces, the 961 kHz field has more gradients and focal spots.

The acoustophoretic devices of the present disclosure create a three dimensional pressure field which includes standing waves perpendicular to the fluid flow. The pressure gradients are large enough to generate acoustophoretic forces orthogonal to the standing wave direction (i.e., the acoustophoretic forces are parallel to the fluid flow direction) which are of the same order of magnitude as the acoustophoretic forces in the wave direction. This permits better particle trapping and collection in the flow chamber and along well-defined trapping lines, as opposed to merely trapping particles in collection planes as in conventional devices. The particles have significant time to move to nodes or anti-nodes of the standing waves, generating regions where the particles can concentrate, agglomerate, and/or coalesce.

In some embodiments, the fluid flow has a Reynolds number of up to 500, i.e. laminar flow is occurring. For practical application in industry, the Reynolds number is usually from 10 to 500 for the flow through the system. The particle movement relative to the fluid motion generates a Reynolds number much less than 1.0. The Reynolds number represents the ratio of inertial flow effects to viscous effects in a given flow field. For Reynolds numbers below 1.0, viscous forces are dominant in the flow field. This results in significant damping where shear forces are predominant throughout the flow. This flow where viscous forces are dominant is called Stokes flow. The flow of molasses is an example.

Wall contouring and streamlining have very little importance to the flow of very viscous fluids or the flow in very tiny passages, like MEMS devices. The flow of the particles relative to the fluid in MEMS devices will be Stokes flow because both the particle diameters and the relative velocities between the particles and fluid are very small. On the other hand, the Reynolds number for the flow through the present system will be much greater than 1.0 because the fluid velocity and inlet diameter are much larger. For Reynolds numbers much greater than 1.0, viscous forces are dominant only where the flow is in contact with the surface. This viscous region near the surface is called a boundary layer and was first recognized by Ludwig Prandtl. In duct flow, the flow will be laminar if the Reynolds number is significantly above 1.0 and below 2300 for fully developed flow in the duct. The flow velocity starts off uniform. As the flow moves down the duct, the effect of wall viscous forces will diffuse inward towards the centerline to generate a parabolic velocity profile. This parabolic profile will have a peak value that is twice the average velocity. The length required for the parabolic profile to develop is a function of the Reynolds number. For a Reynolds number of 20, the development length will be 1.2 duct diameters. Thus, fully developed flow happens very quickly. This peak velocity in the center can be detrimental to acoustic particle separation. Also, turbulence can occur and so flow surface contouring is very important in controlling the flow. Thus, the shape of the contoured nozzle wall will have a large effect on the final velocity profile. The area convergence increases the flow average velocity, but it is the wall contour that determines the velocity profile. The nozzle wall contour will be a flow streamline, and is designed with a small radius of curvature.

The transducer(s) is/are used to create a pressure field that generates forces of the same order of magnitude both orthogonal to the standing wave direction and in the standing wave direction. When the forces are roughly the same order of magnitude, particles of size 0.1 microns to 300 microns will be moved more effectively towards regions of agglomeration ("trapping lines"). Because of the equally large gradients in the orthogonal acoustophoretic force component, there are "hot spots" or particle collection regions that are not located in the regular locations in the standing wave direction between the transducer and the reflector. Such hot spots are located in the maxima or minima of acoustic radiation potential. Such hot spots represent particle collection locations which allow for better wave transmission between the transducer and the reflector during collection and stronger inter-particle forces, leading to faster and better particle agglomeration.

One application of the acoustophoretic separator is separation of cells from a medium, such as the separation of red blood cells, described in U.S. application Ser. No. 13/866, 584 to Dutra and Lipkens, entitled "ACOUSTOPHORETIC SEPARATION OF LIPID PARTICLES FROM RED BLOOD CELLS," the entirety of which is hereby fully incorporated by reference.

Another application is the separation of a biological therapeutic protein from the biologic cells that produce the protein. In this regard, current methods of separation require filtration or centrifugation, either of which can damage cells, releasing protein debris and enzymes into the purification process and increasing the load on downstream portions of the purification system. It is desirable to be able to process volumes having higher cell densities, because this permits collection of larger amounts of the therapeutic protein and better cost efficiencies.

Figure 10B:
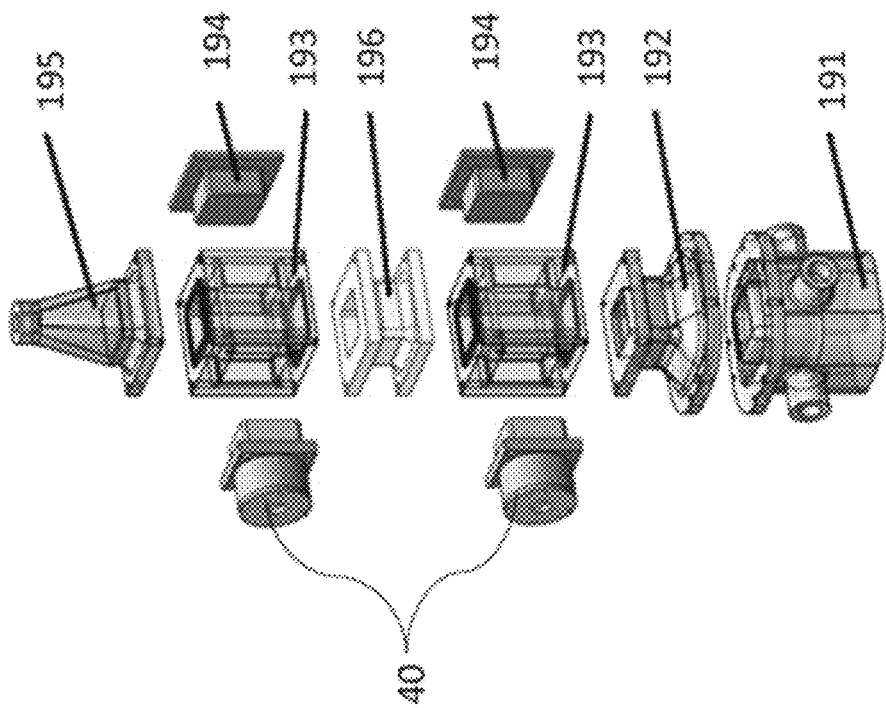
FIG. 10B shows an exploded view of a stacked acoustophoretic separator with two acoustic chambers.
Figure 10A:
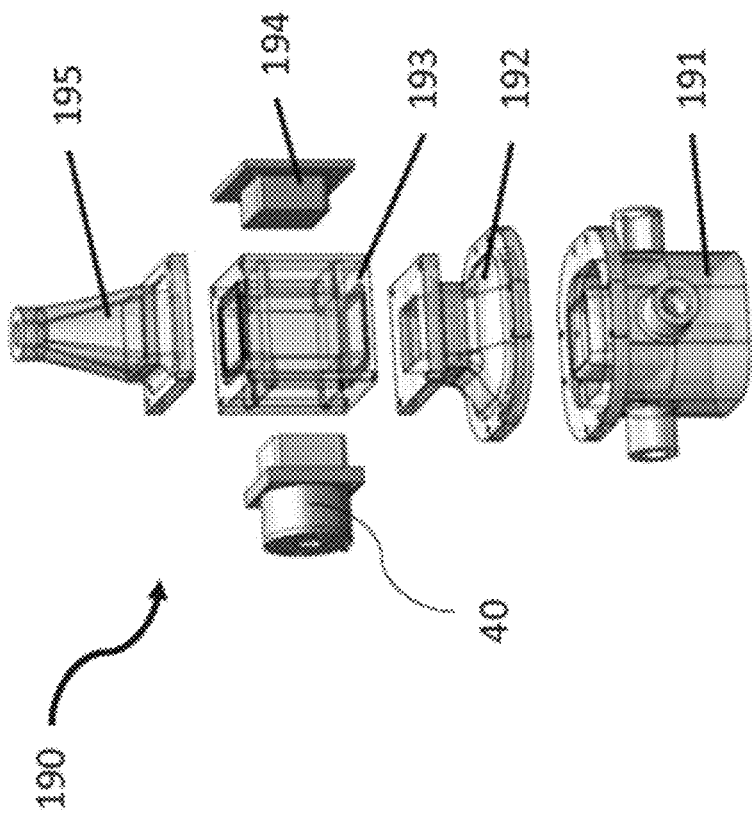
FIG. 10A shows an exploded view of an acoustophoretic separator used in Bio-Pharma applications.

FIG. 10A and FIG. 10B are exploded views showing the various parts of acoustophoretic separators. FIG. 10A has only one separation chamber, while FIG. 10B has two separation chambers.

Referring to FIG. 10A, fluid enters the separator 190 through a four-port inlet 191. A transition piece 192 is provided to create plug flow through the separation chamber 193. A transducer 40 and a reflector 194 are located on opposite walls of the separation chamber. Fluid then exits the separation chamber 193 and the separator through outlet 195.

FIG. 10B has two separation chambers 193. A system coupler 196 is placed between the two chambers 193 to join them together.

Acoustophoretic separation has been tested on different lines of Chinese hamster ovary (CHO) cells. In one experiment, a solution with a starting cell density of $8.09 \times 10^6$ cells/mL, a turbidity of 1,232 NTU, and cell viability of roughly 75% was separated using a system as depicted in FIG. 10A. The transducers were 2 MHz crystals, run at approximately 2.23 MHz, drawing 24-28 Watts. A flow rate of 25 mL/min was used. The result of this experiment is shown in FIG. 11A.

In another experiment, a solution with a starting cell density of $8.09 \times 10^6$ cells/mL, a turbidity of 1,232 NTU, and cell viability of roughly 75% was separated. This CHO cell line had a bi-modal particle size distribution (at size 12 μm and 20 μm). The result is shown in FIG. 11B.

Figure 11A:
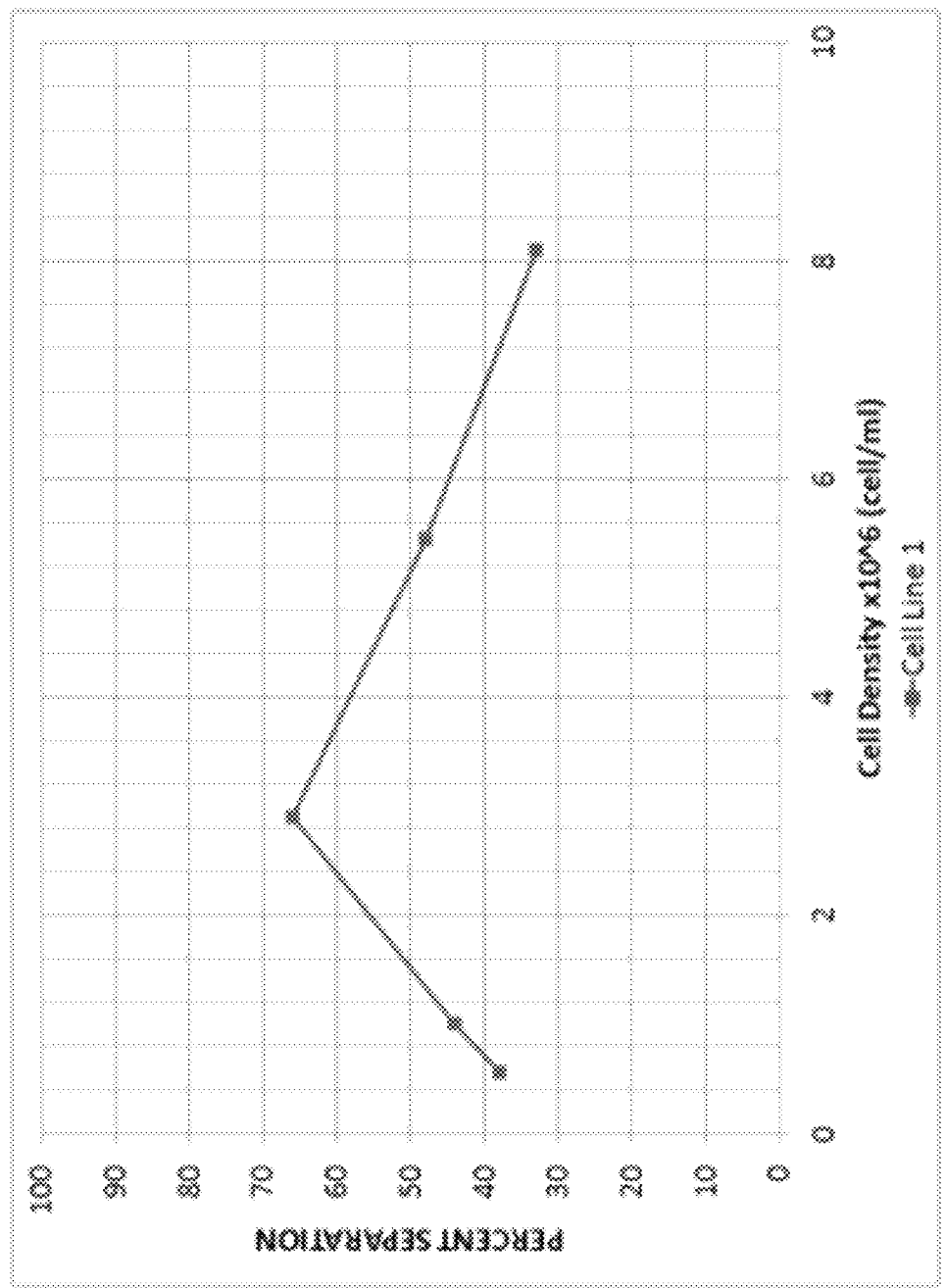
FIG. 11A is a graph showing the efficiency of removing cells from a medium using a Beckman Coulter Cell Viability Analyzer for one experiment.
Figure 11B:
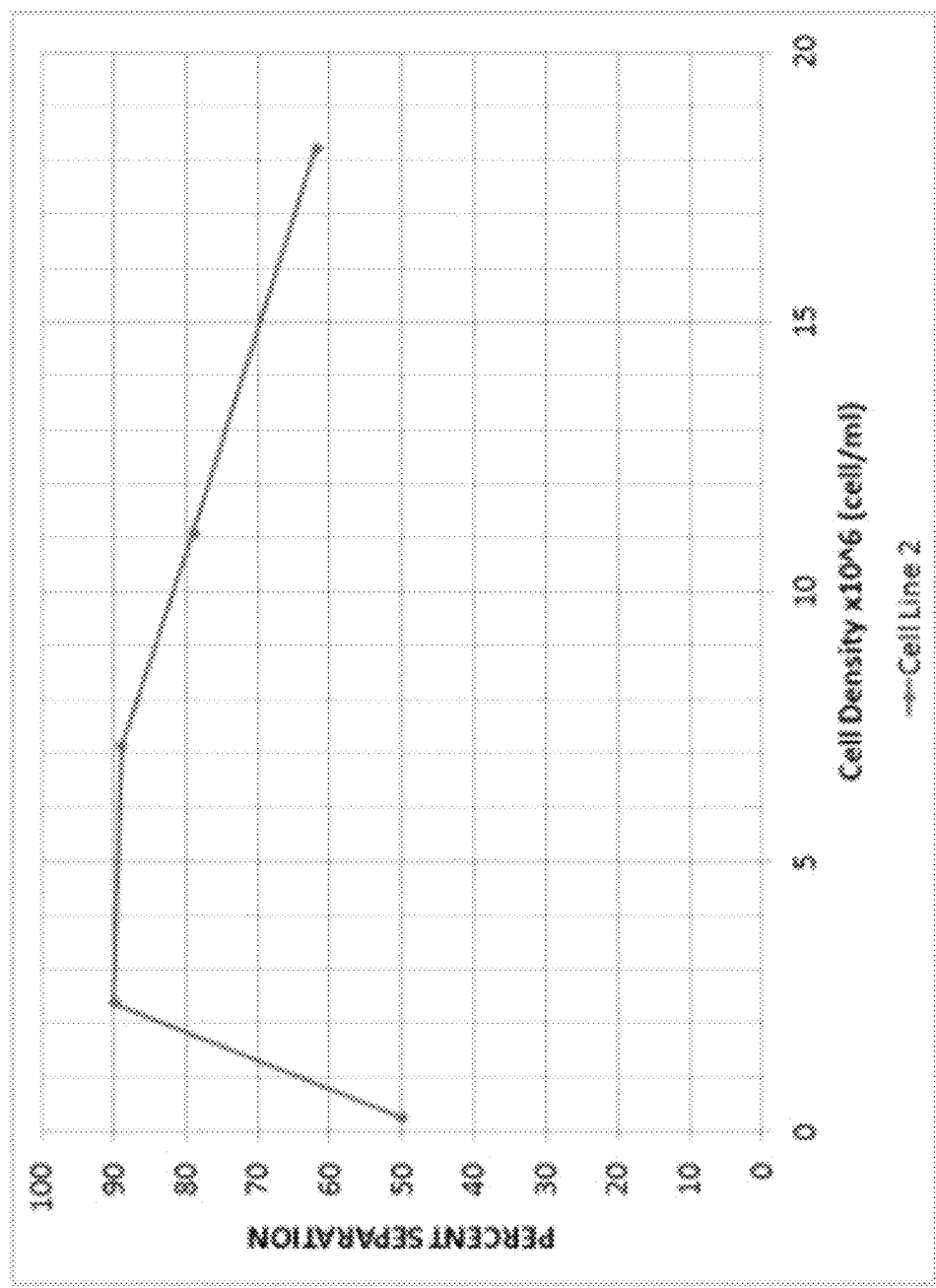
FIG. 11B is a graph showing the efficiency of removing cells from a medium using a Beckman Coulter Cell Viability Analyzer for another experiment.

FIG. 11A and FIG. 11B were produced by a Beckman Coulter Cell Viability Analyzer. Other tests revealed that frequencies of 1 MHz and 3 MHz were not as efficient as 2 MHz at separating the cells from the fluid.

In other tests at a flow rate of 10 L/hr, 99% of cells were captured with a confirmed cell viability of more than 99%. Other tests at a flow rate of 50 mL/min (i.e. 3 L/hr) obtained a final cell density of $3 \times 10^6$ cells/mL with a viability of nearly 100% and little to no temperature rise. In yet other tests, a 95% reduction in turbidity was obtained at a flow rate of 6 L/hr.

Testing on a scaled unit was performed using yeast as a simulant for CHO for the biological applications. For these tests, at a flow rate of 15 L/hr, various frequencies were tested as well as power levels. Table 1 shows the results of the testing.

TABLE 1

| 2.5" × 4" System results at 15 L/hr Flow rate | | | |
|---|---|---|---|
| Frequency (MHz) | 30 Watts | 37 Watts | 45 Watts |
| 2.2211 | 93.9 | 81.4 | 84.0 |
| 2.2283 | 85.5 | 78.7 | 85.4 |
| 2.2356 | 89.1 | 85.8 | 81.0 |
| 2.243 | 86.7 | — | 79.6 |

In biological applications, many parts, e.g. the tubing leading to and from the housing, inlets, exit plenum, and entrance plenum, may all be disposable, with only the transducer and reflector to be cleaned for reuse. Avoiding centrifuges and filters allows better separation of the CHO cells without lowering the viability of the cells. The form factor of the acoustophoretic separator is also smaller than a filtering system, allowing the CHO separation to be miniaturized. The transducers may also be driven to create rapid pressure changes to prevent or clear blockages due to agglomeration of CHO cells. The frequency of the transducers may also be varied to obtain optimal effectiveness for a given power.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An acoustophoresis device, comprising:
   one or more device inlets at a bottom end of the device, the bottom end having a first diameter for receiving fluid flow;
   a contoured wall above the inlet that narrows the fluid flow to a second diameter of a connecting duct;
   a flow chamber above the connecting duct, the flow chamber having:
   an inlet at a bottom end for receiving the fluid flow,
   an outlet at a top end opposite the bottom end,
   at least one ultrasonic transducer located on a wall of the flow chamber, the ultrasonic transducer including a piezoelectric material driven by a voltage signal to create a multi-dimensional standing wave in the flow chamber, and
   a reflector located on a wall on the opposite side of the flow chamber from the at least one ultrasonic transducer;
   a first device outlet located at the bottom end of the device and separated from the device inlet by a longitudinal sidewall; and
   a second device outlet located at the top end of the device above the flow chamber outlet.

2. The device of claim 1, wherein the device includes a plurality of device inlets spaced about the bottom end of the device, and the longitudinal sidewall is spaced apart from the contoured wall.

3. The device of claim 1, wherein the piezoelectric material of the at least one ultrasonic transducer has a rectangular shape.

4. The device of claim 1, wherein the reflector has a non-planar surface.

5. The device of claim 1, wherein the first device outlet located at the bottom end of the device has a conical shape with a cross-sectional area that is most narrow at the bottom of the device.

6. The device of claim 1, wherein the multi-dimensional standing wave results in an acoustic radiation force having an axial force component and a lateral force component that are of the same order of magnitude.

7. The device of claim 1, wherein the transducer comprises:
   a housing having a first end, a second end, and an interior volume; and
   a crystal at the second end of the housing having an exposed exterior surface and an interior surface, the crystal being able to vibrate when driven by a voltage signal.

8. The device of claim 1, wherein no backing layer is present within the housing of the transducer, and an air gap is present in the interior volume between the crystal and a plate at the first end of the housing.

9. The device of claim 1, wherein the transducer further comprises a backing layer contacting the interior surface of the crystal, the backing layer being made of a substantially acoustically transparent material.

10. The device of claim 9, wherein the substantially acoustically transparent material is balsa wood, cork, and foam.

11. The device of claim 9, wherein the substantially acoustically transparent material has a thickness of up to 1 inch.

12. The device of claim 1, wherein the flow chamber further comprises a transparent window for viewing the interior of the flow chamber.

13. The device of claim 1, wherein the device has a length L from the at least one device inlet to a bottom of the longitudinal sidewall, and a ratio of the length L to the first diameter is less than 1.

14. The device of claim 1, wherein the flow chamber has a plurality of the ultrasonic transducers located on the wall of the flow chamber.

15. A method of separating biological cells from a host fluid, comprising:
flowing a mixture of the host fluid and the biological cells upwards through an apparatus, the apparatus comprising:
a flow chamber having at least one inlet and at least one outlet;
at least one ultrasonic transducer located on a wall of the flow chamber, the transducer including a piezoelectric material driven by a voltage signal to create a multi-dimensional standing wave in the flow chamber; and
a reflector located on the wall on the opposite side of the flow chamber from the at least one ultrasonic transducer; and
sending a pulsed voltage signal to drive the at least one ultrasonic transducer to separate the host fluid from the biological cells;
wherein the multi-dimensional standing wave results in an acoustic radiation force having an axial force component and a lateral force component that are of the same order of magnitude.

16. The method of claim 15, wherein the biological cells are Chinese hamster ovary (CHO) cells, NS0 hybridoma cells, baby hamster kidney (BHK) cells, or human cells.

17. The method of claim 15, wherein the mixture flows vertically upwards, and the biological cells sink downward to a collection duct.

18. The method of claim 15, wherein the mixture flows from an apparatus inlet through an annular plenum and upwards past a contoured nozzle wall prior to entering the flow chamber inlet.

19. The method of claim 18, wherein the separated biological cells agglomerate and sink, and wherein the inflowing mixture is directed to the sinking biological cells by the contoured nozzle wall.

20. The method of claim 15, wherein the mixture of the host fluid and the biological cells has a Reynolds number of 1500 or less prior to entering the flow chamber.

21. The acoustophoresis device of claim 1, wherein the multidimensional standing wave operates in a tumbling fashion.

22. An acoustophoresis device, comprising:
one or more device inlets at a bottom end of the device, which lead to a flow chamber through which a fluid is flowed;
at least one ultrasonic transducer coupled to the flow chamber and a reflector located opposite the at least one ultrasonic transducer, the at least one ultrasonic transducer including a piezoelectric material configured to be driven to generate a multi-dimensional acoustic standing wave in the flow chamber;
a first device outlet located at the bottom end of the device and separated from the one or more device inlets by a longitudinal sidewall; and
a second device outlet located at a top end of the device above the flow chamber;
wherein the device is configured to operate in a continuous process in which particles that are entrained in the fluid are continuously trapped and removed.

* * * * *